(12) United States Patent
Eggert-Richter et al.

(10) Patent No.: US 11,937,043 B2
(45) Date of Patent: Mar. 19, 2024

(54) ANTENNA FOR PROTECTIVE PERSONAL EQUIPMENT

(71) Applicant: 3M INNOVATIVE PROPERTIES COMPANY, St. Paul, MN (US)

(72) Inventors: Sebastian Eggert-Richter, Wülfrath (DE); Michael H. Stalder, Uedem (DE); Christian Weinmann, Alsdorf (DE); Benhard C. Schneider, Herne (DE); Paul H. R. Jolly, Hants (GB)

(73) Assignee: 3M Innovative Properties Company, St. Paul, MN (US)

( * ) Notice: Subject to any disclaimer, the term of this patent is extended or adjusted under 35 U.S.C. 154(b) by 262 days.

(21) Appl. No.: 17/621,438

(22) PCT Filed: Jun. 23, 2020

(86) PCT No.: PCT/IB2020/055912
§ 371 (c)(1),
(2) Date: Dec. 21, 2021

(87) PCT Pub. No.: WO2020/261110
PCT Pub. Date: Dec. 30, 2020

(65) Prior Publication Data
US 2022/0360884 A1 Nov. 10, 2022

Related U.S. Application Data

(60) Provisional application No. 62/868,391, filed on Jun. 28, 2019.

(51) Int. Cl.
*H04R 1/10* (2006.01)
*H04W 4/029* (2018.01)

(52) U.S. Cl.
CPC ......... *H04R 1/1083* (2013.01); *H04R 1/1008* (2013.01); *H04W 4/029* (2018.02); *H04R 2420/07* (2013.01)

(58) Field of Classification Search
CPC ................ H04R 1/1083; H04R 1/1008; H04R 2420/07; H04R 2225/025; H04R 2225/51; H04R 25/65
See application file for complete search history.

(56) References Cited

U.S. PATENT DOCUMENTS

| | | | |
|---|---|---|---|
| 7,676,242 B2 | 3/2010 | Siddiqui | |
| 9,425,502 B2 | 8/2016 | Chen | |
| 2018/0070179 A1* | 3/2018 | McAuliffe | ............. H05K 1/147 |

FOREIGN PATENT DOCUMENTS

| | | |
|---|---|---|
| CN | 101770599 | 7/2010 |
| CN | 205179302 | 4/2016 |

(Continued)

OTHER PUBLICATIONS

International Search Report for PCT International Application No. PCT/IB2020/055912, dated Sep. 8, 2020, 5 pages.

*Primary Examiner* — Sunita Joshi
(74) *Attorney, Agent, or Firm* — Katherine M. Scholz

(57) ABSTRACT

A hearing protection device is provided. The hearing protection device includes a first earmuff connected to a second earmuff by a headband. Each of the first and second earmuffs are configured to dampen ambient sound. The hearing protection device also includes an antenna, located within a housing of the first earmuff. The antenna comprises a rigid portion coupled to a flexible portion. Both the rigid portion and the flexible portion are fixed within the housing. The flexible portion is configured to remain substantially in line with a ground plane with respect to the rigid portion.

20 Claims, 12 Drawing Sheets

(56) References Cited

FOREIGN PATENT DOCUMENTS

| | | | | |
|---|---|---|---|---|
| CN | 208820046 | | 5/2019 | |
| CN | 208820046 U | * | 5/2019 | ............ H01Q 1/273 |
| JP | 2003-087022 | | 3/2003 | |
| JP | 2003087022 A | * | 3/2003 | |
| JP | 2007-235215 | | 9/2007 | |
| JP | 2013-162452 | | 8/2013 | |
| WO | WO 2016-039904 | | 3/2016 | |
| WO | WO 2016-200950 | | 12/2016 | |

* cited by examiner

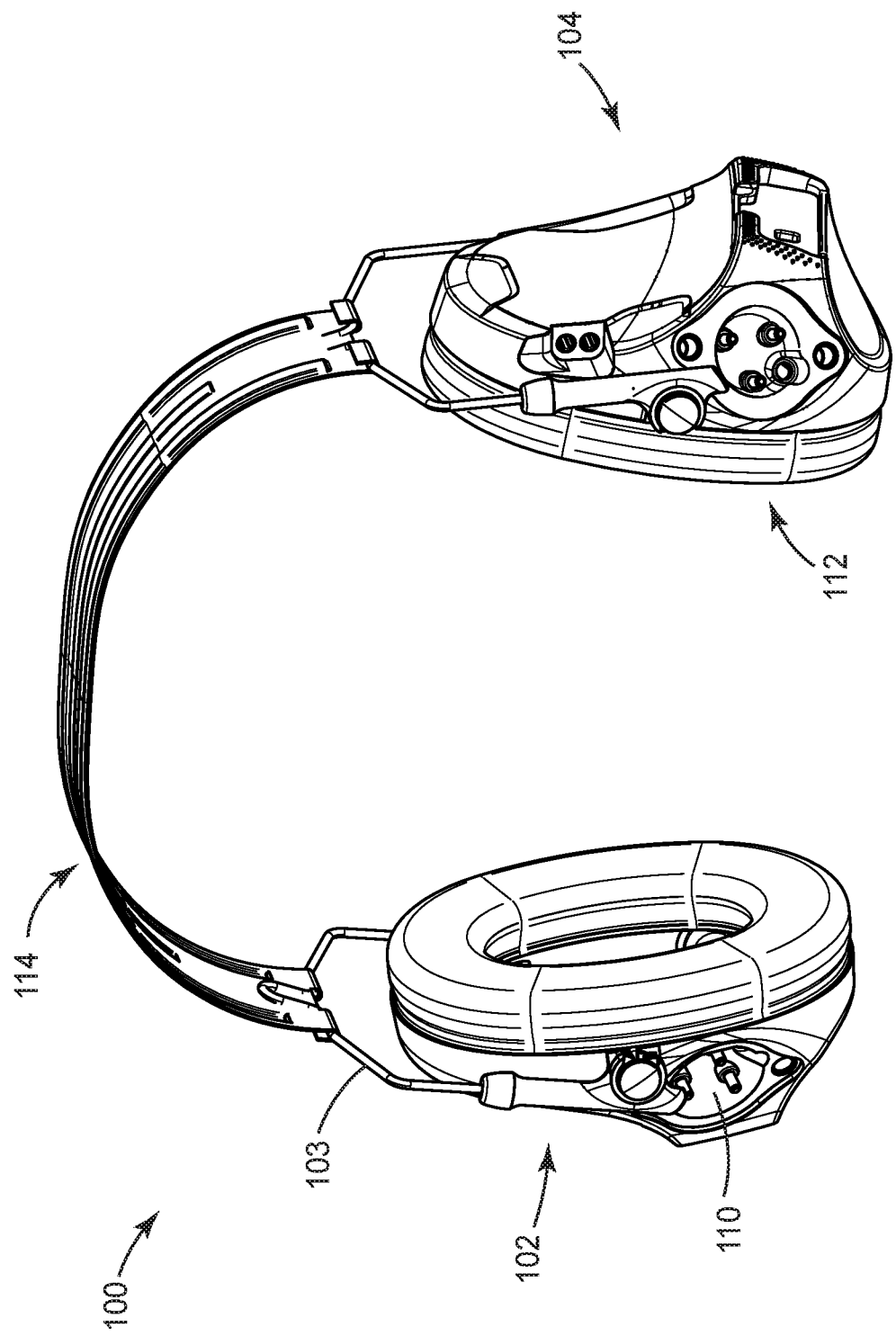

ANTENNA FOR PROTECTIVE PERSONAL EQUIPMENT

CROSS REFERENCE TO RELATED APPLICATIONS

This application is a national stage filing under 35 U.S.C. 371 of PCT/IB2020/055912, filed Jun. 23, 2020, which claims the benefit of U.S. Provisional Application No. 62/868,391, filed Jun. 28, 2019, the disclosure of which is incorporated by reference in its/their entirety herein.

BACKGROUND

The use of hearing devices are well known. Many hearing devices involve an antenna configured to receive radio frequencies (RF) which is then demodulated to produce (possibly with other information) a sound signal that can be provided to a user through a speaker. Hearing devices often come in the form of in-ear plugs or over-the-ear headsets. Sound quality and consistency have been issues facing construction of new hearing devices.

SUMMARY

A hearing protection device is provided. The hearing protection device includes a first earmuff connected to a second earmuff by a headband. Each of the first and second earmuffs are configured to dampen ambient sound. The hearing protection device also includes an antenna, located within a housing of the first earmuff. The antenna comprises a rigid portion coupled to a flexible portion. The rigid portion and the flexible portion are retained within the housing this may be provided using an attachment mechanism or applied pressure.

BRIEF DESCRIPTION OF THE DRAWINGS

The drawings illustrate generally, by way of example, but not by way of limitation, various embodiments discussed in the present document.

FIGS. 1A-1D illustrate a headset and components in which preferred embodiments of the present invention may be included.

DETAILED DESCRIPTION

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

In the methods described herein, the acts can be carried out in any order without departing from the principles of the disclosure, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

Personal Protective Equipment (PPE) often includes a headset with a set of over-the-ear hearing protection devices, often referred to as ear muffs. However, while a headset is illustrated and described, it is explicitly contemplated that other configurations may be possible. For example, FIG. 1A illustrates a headset with a headband connecting two earmuffs. However, a connection may also include a neckband, in some embodiments. Each ear muff is configured to dampen ambient environmental sounds, but also includes electronic circuitry configured to pick up ambient sounds and reproduce them, through internal speakers, at a sound level safe for a user. However, it is important that radio frequencies (RF) containing at least sound information received and transmitted through electronic means be reproduced as close to nature as possible. In order to do this, an antenna for a hearing protection device needs to have an (RF) omnidirectional radiation pattern with little gain deviation. This allows the hearing protection device to be part of a Natural Interaction Behavior (NIB) communication system.

Figure 1B:
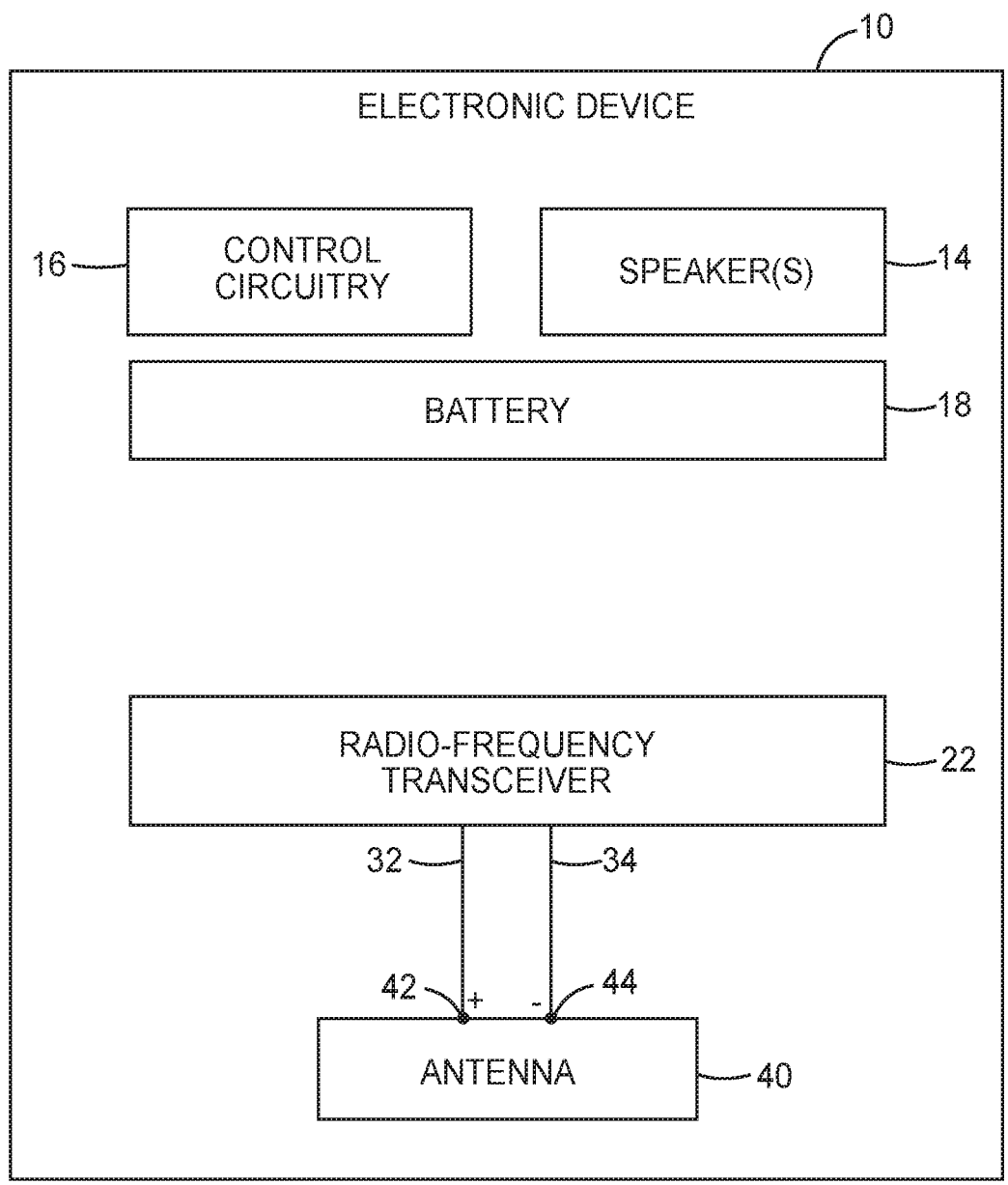

FIGS. 1A-1D illustrate a headset and components in which preferred embodiments of the present invention may be included. FIG. 1A illustrates a headset in which preferred embodiments of the present invention may be included. Headset 100 includes two over-the-ear hearing protection devices 102 and 104 connected by a headband 114. Hearing protector devices 102 are mechanically connected by headband 114, which may in a preferred embodiment of the invention also include padding for user comfort 112. The mechanical connection may include one or more metallic spring wires 103 to keep hearing protection devices 102 in place by applying a certain pressure to the human head. The spring wires can be supported by a sheet of metal or plastic encased in a soft material which also acts like a cushion to enhance comfort for the user while wearing headset 100.

Each hearing protector device 102 includes a microphone 110, which in a preferred embodiment may be configured such that wind noise is reduced. Additionally, each hearing protector device 102 may in a preferred embodiment also include cushioning 112 which may be configured to both increase user comfort and dampen ambient sounds.

FIG. 1B illustrates a schematic diagram of components for a hearing protection device 10. Hearing protection device 10 may in a preferred embodiment be similar to one of hearing protector devices 102, illustrated in FIG. 1A. Device 10 may include control circuitry such as storage and processing circuitry 16. Storage and processing circuitry 16 may include storage such as nonvolatile memory (e.g., flash memory or other electrically-programmable-read-only memory configured to form a solid state drive), volatile memory (e.g., static or dynamic random-access-memory), etc. Processing circuitry in storage and processing circuitry 16 may be used to control the operation of device 10. This processing circuitry may be based on one or more microprocessors, microcontrollers, digital signal processors, baseband processor integrated circuits, application specific integrated circuits, or other such devices as known to those practiced in the art.

Storage and processing circuitry 16 may be used to run software on device 10. The software may handle communications, may process sensor signals and take appropriate action based on the processed sensor signals (e.g., to turn on or off functions in device 10, to start or stop audio playback, etc.), and may handle other device operations. To support interactions with other PPE equipment, storage and processing circuitry 16 may be used in implementing communications protocols. Communications protocols that may be implemented using storage and processing circuitry 16 include wireless local area network protocols (e.g., IEEE 802.11 protocols—sometimes referred to as WiFi® and WiGig), protocols for other short-range wireless communications links such as the Bluetooth® protocol, cellular telephone protocols, as well as others known to those practiced in the art. For example, the protocol described in WO 2016/200950, published on Dec. 15, 2016, which is incorporated herein by reference, may be used in some embodiments.

Device 10 may include microphones, speakers, tone generators, and other audio components (see, e.g., one or more speakers 14). Microphones may gather voice signals and/or ambient noise signals. Speakers may play back sound for a user either at ambient levels or after being processed by control circuitry 16.

Device 10 may include battery 18 to provide power to the circuitry of device 10. Battery 18 may be a rechargeable battery, chargeable either in a wired or wireless configuration. In another embodiment, battery 18 is not be a rechargeable battery.

Electronic device 10 may also include radio-frequency transceiver 22 and one or more antennas such as antenna 40. Antenna 40 may have a feed that includes positive antenna feed terminal 42 and ground antenna feed terminal 44. Transmission line 30 may be used to couple radio-frequency transceiver circuitry 22 to antenna 40. Transmission line 30 may have a positive signal path such as line 32 and a ground signal path such as line 34. Transmission lines in device 10 such as transmission line 30 may include coaxial cable paths, microstrip transmission lines, stripline transmission lines, edge-coupled microstrip transmission lines, edge-coupled stripline transmission lines, transmission lines formed from combinations of transmission lines of these types, etc. Filter circuitry, switching circuitry, impedance matching circuitry, and other circuitry may be interposed within the transmission lines, if desired. The connections to the antenna or to a plurality of antennas may use an unbalanced transmission line for each antenna the transmission line may include filter circuitry, switching circuitry, impedance matching networks and other items known to those practiced in the art.

The construction and design of antenna 40 is important for the function of a hearing protection device that is part of a personal protection equipment system. Specifically, antenna 40 must have a reliable electrical connection for steady performance. Performance should also be repeatable from device to device. It is also desired to remove screws and solder as attachment mechanisms of the antenna within a housing. This both reduces cost of manufacturing and also ensures that unwanted connections are less likely and that electrical connections are also more stable during the life of the hearing protection device.

Figure 1C:
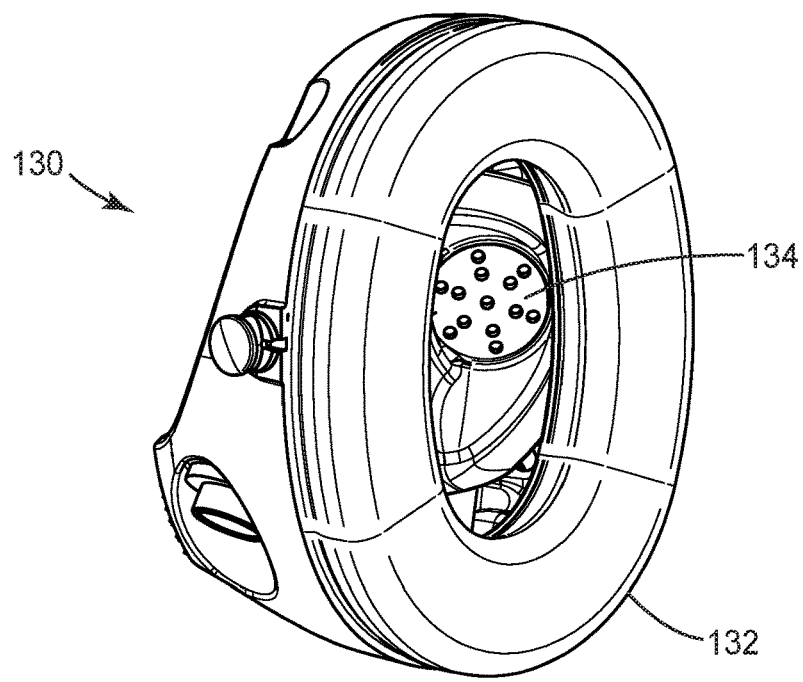

FIG. 1C illustrates a hearing protector device 130 in isolation from a headband 114. In some embodiments, only one hearing protector device 130 includes an antenna (not shown in FIG. 1B). Hearing protector device 130 includes cushioning 132, and a speaker 134, configured to provide reproduced sound to a user.

Figure 1D:
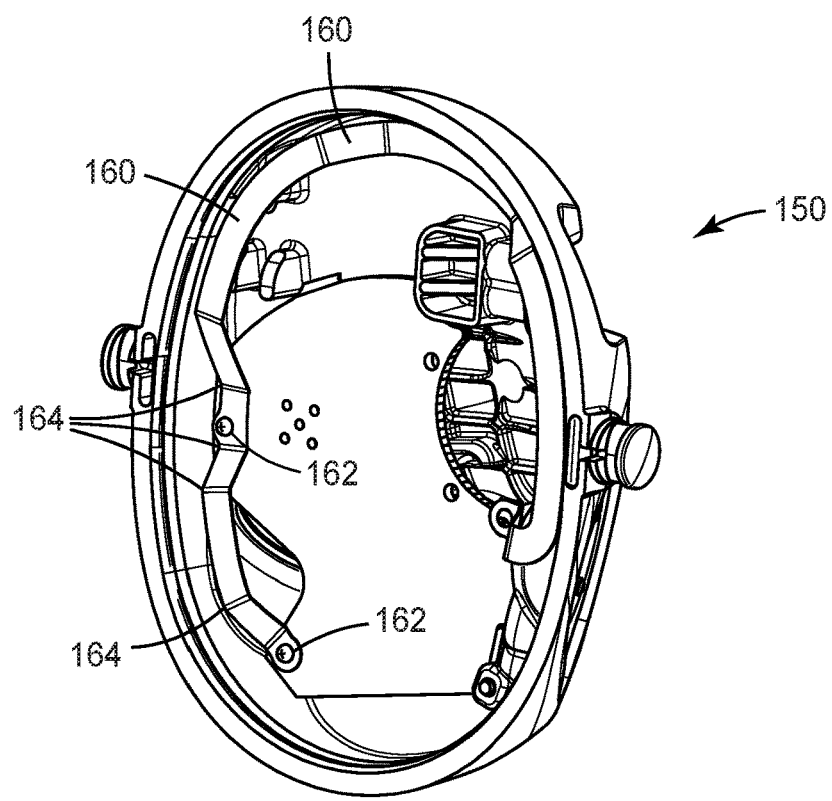

FIG. 1D illustrates a hearing protector device 150 with an antenna 160. As illustrated in FIG. 1C, antenna 160 may be bent at several locations 164 within the hearing protector housing. In addition, several screws 162 may be required to fix the hearing protector device in place.

As discussed with respect to FIGS. 1B-1D, each headset is equipped with an antenna and a transceiver chipset. The antenna should be designed to have an omnidirectional radiation pattern with little gain deviation. In a preferred embodiment, the antenna can be configured to work with NIB technology, such that the receiving signal strength may be used to determine the distance between users wearing different headsets. From the distance a volume level may be derived, so that users moving apart will perceive the sound level being attenuated with increasing distance.

In one preferred embodiment, the antenna is integrated into one of the headset's cups only. This can reduce the cost of manufacturing the headset, but increases the difficulty of providing natural-sounding reproduced sound as the antenna needs to receive signals in a 360° range around a user's head. This requires the antenna to work properly with a human head blocking a portion of the range. Proper position and design of the antenna within the housing of a hearing protection device is, therefore, crucial. It is also important that the antenna remain in place within the hearing protection device, without significant movement within the housing. In one embodiment, the antenna is located in the top half of the earmuff, when the headset is worn by a user. Such positioning may help to counteract the interference caused by the wearer's head and allow the antenna to have better reception. While a single antenna is contemplated in many embodiments described herein, in other embodiments it is contemplated that a second antenna is present in a second earmuff.

Proper assembly and electrical connection of the antenna to the transceiver electronics is vital to achieve a repeatable and reliable antenna performance. In common solutions this electrical contact is realized with RF connectors. Unfortunately, such (miniaturized) connectors are not suitable for the harsh environmental conditions present in some applications, such as military applications. Soldering is known to work, but it has certain disadvantages, as the quality of the soldering joint varies with the personnel in production. The antenna performance and thus the NIB functionality requires a stable electrical connection and little to no impedance mismatch between antenna and transceiver electronics.

Figure 2:
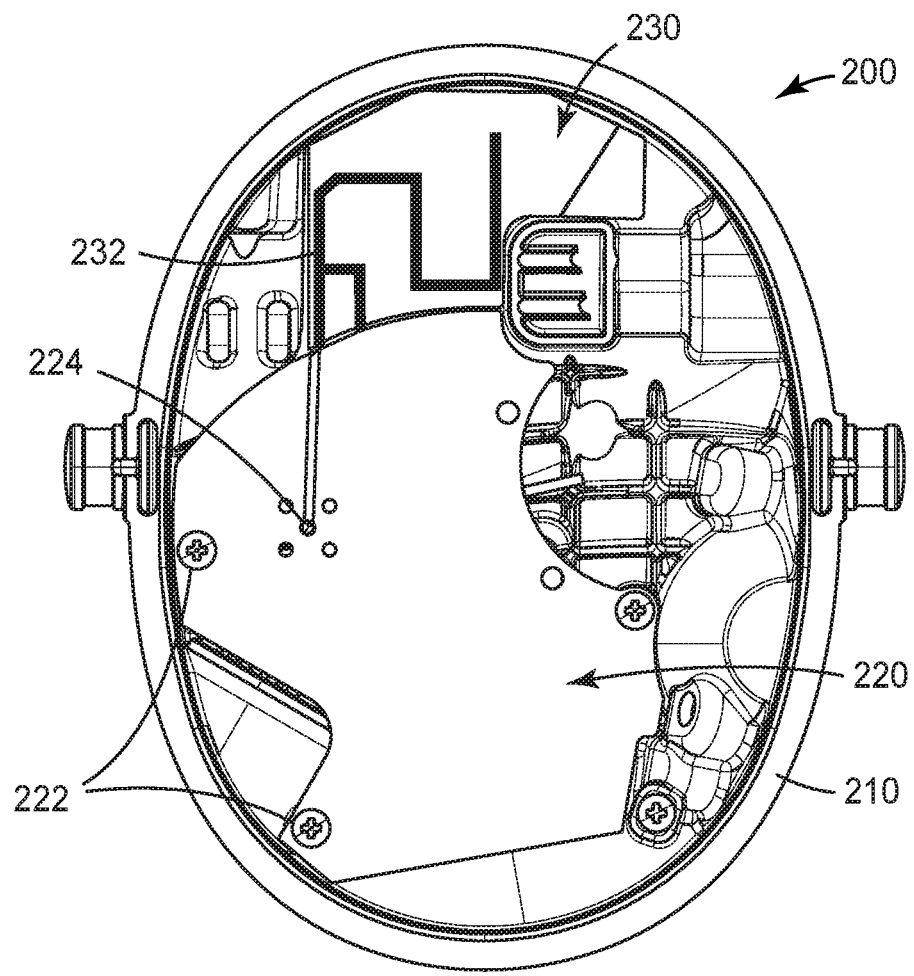
FIG. 2 illustrates a preferred embodiment of a headset antenna in accordance with the present invention.

FIG. 2 illustrates a test headset antenna in accordance with a preferred embodiment of the present invention. The exterior of the headset is removed for convenience. Antenna 230 is housed within hearing protection device in an internal housing 210 for electronics (partially shown in FIG. 2). The antenna has a rigid portion 220 and a flexible portion 230.

Rigid portion 220 is held in place by one or more screws 222, in one preferred embodiment. Flexible portion 230 is held in place, in one preferred embodiment, by adhesive. Electronics for a hearing protection device are configured to connect at connection point 224. Conductive element 232 is laminated onto the flexible portion 230 as illustrated in FIG. 2. In one embodiment, conductive element 232 is copper.

Antenna 230, in a preferred embodiment, includes a planar conductive element laminated onto a flexible substrate material. The flexible material may be, for example, polyimide. However, other suitable materials are also envisioned. Flexible portion 230, in a preferred embodiment, is part of, and extends from, rigid portion 220. In one embodiment, rigid portion 220 is a rigid PCB material. For example, the rigid PCB material may be fire-retardant, such as an FR-4 grade glass fiber and resin laminate. While some bending of flexible portion 230 may take place, antenna system 200 is substantially planar once installed within housing 210.

Figure 3A:
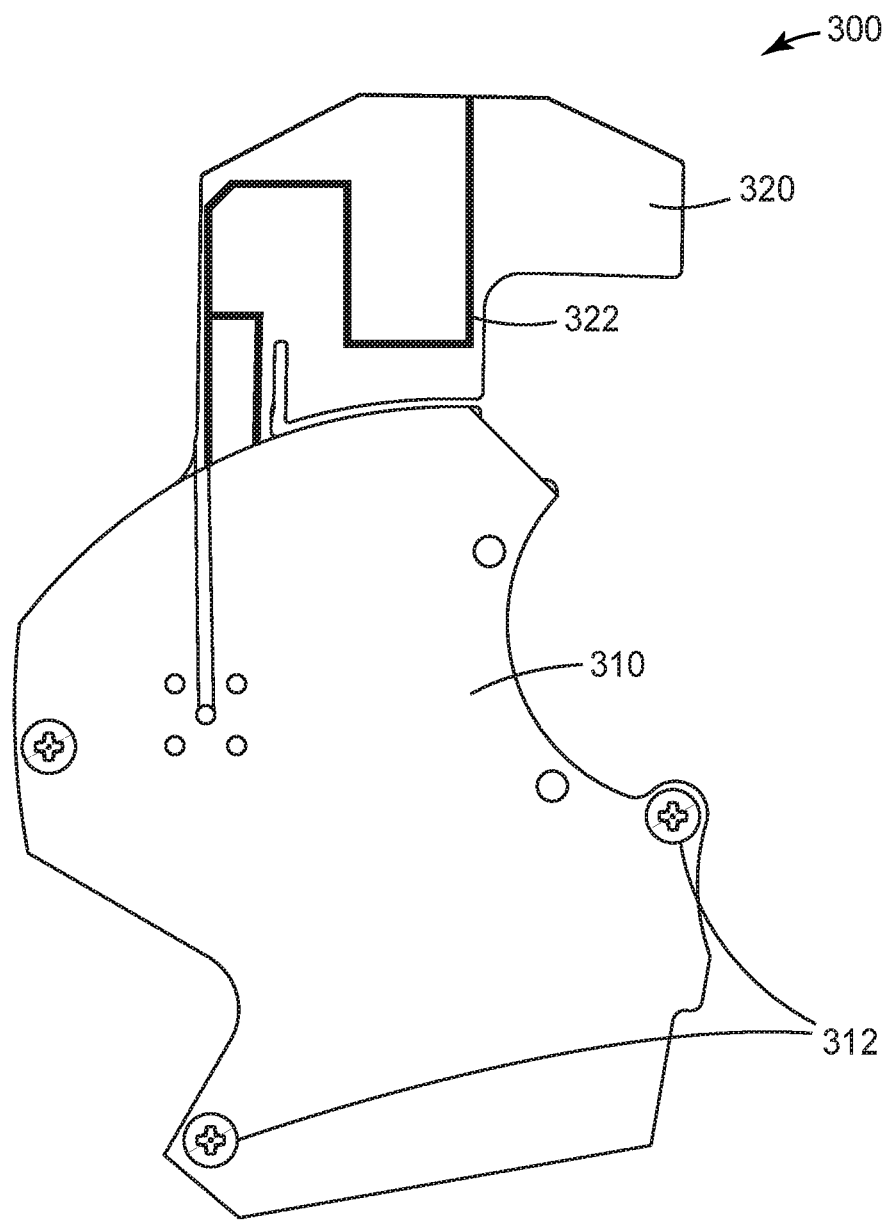
FIGS. 3A-3C illustrate a preferred embodiment of a headset antenna in accordance with a further preferred embodiment of the present invention.
Figure 3B:
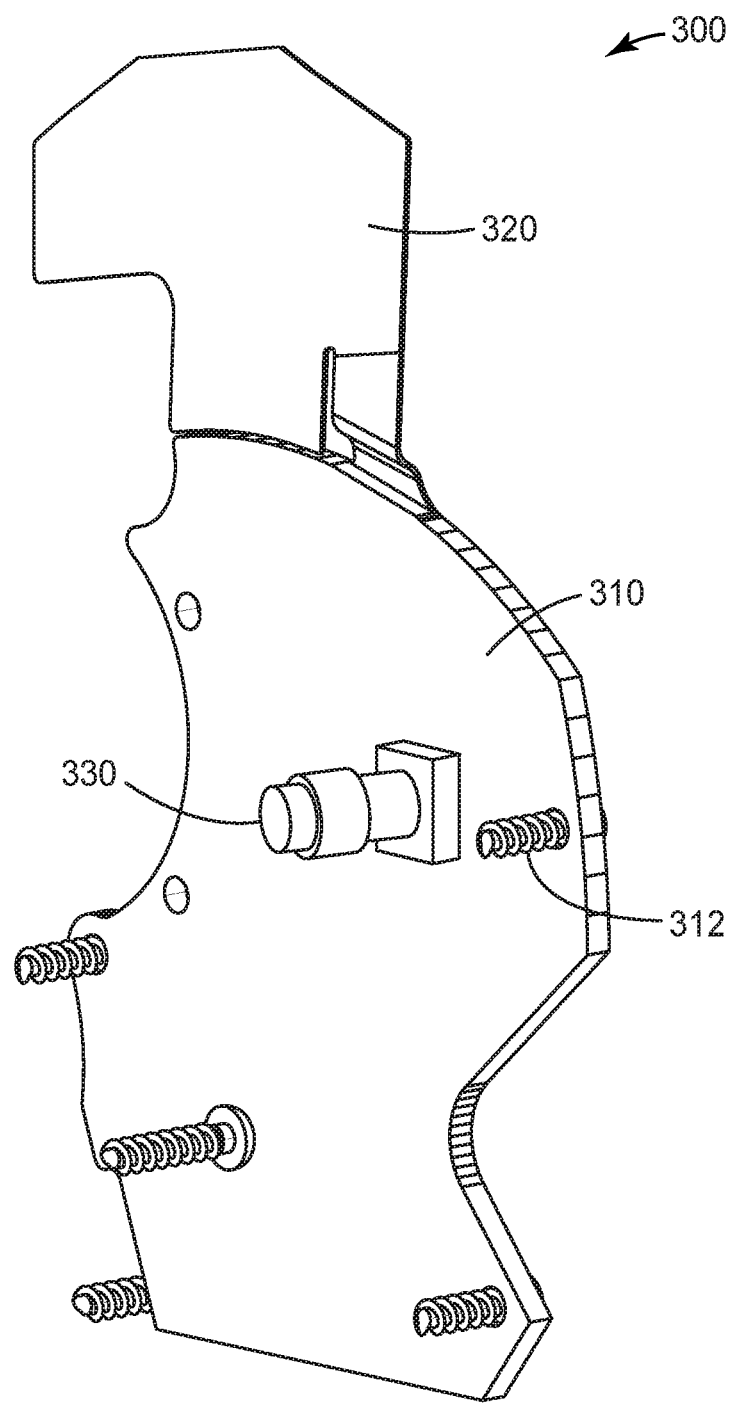
Figure 3C:
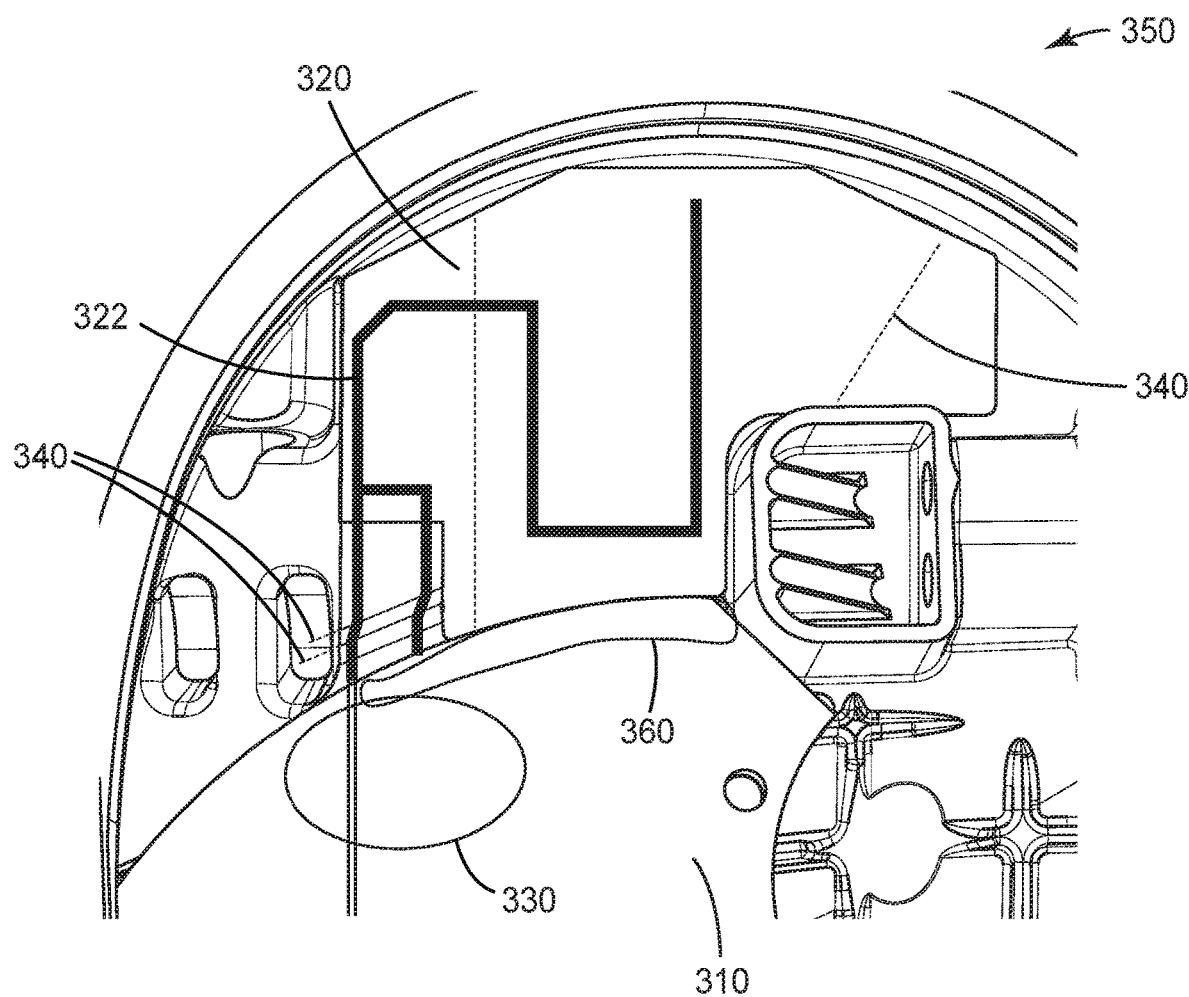

FIGS. 3A-3C illustrate a headset antenna in accordance with another embodiment of the present invention. As illustrated in FIGS. 3A & 3B, antennae 300 is substantially planar after manufacturing, with a flexible portion 320 extending from a rigid portion 310. Rigid portion 310 is intended to be fixed in place using one or more screws 312. However, while screws are illustrated in FIGS. 3A and 3B, other fixing mechanisms could also be used. For example, an interface or insert may be present between rigid portion 310 and the housing such that an applied pressure maintains the position of the rigid portion. In another embodiment, one or more hooks may maintain a position of rigid portion 310.

A conductive element 322 is laminated into one or more layers of flexible portion 320, allowing antennae 300 to function as part of a PPE. The conductive element may include copper, or another suitable electrically conductive element.

As illustrated in view 350 of FIG. 3C, flexible portion 320 is assembled into an internal housing and bent along bend indications 340. However, while some portions experience some bending, flexible portion 320 of antennae remains substantially planar, and substantially completely within the housing of the hearing protection device.

Ground plane 360 extends substantially along an edge of rigid portion 310. It is important that flexible portion 320 remain on an opposite side of ground plane 360, with respect to rigid portion 310. If flexible portion 320 were to bend such that it was parallel to rigid portion 310, or even if it were to bend such that a portion crossed ground plane 360, antennae 300 would not be able to function omnidirectionally. Flexible portion 320 may be able to bend in the three dimensional space above ground plane 360 within the housing during manufacturing, however it is also important that it remain in place during use. Therefore, an adhesive tape layer may be used to maintain placement of flexible portion 320. In one embodiment, the adhesive tape layer comprises an anisotropic electrical conductive adhesive film. This setup is advantageous for several reasons: The electrical connection is easily done without soldering, the impedance of the antenna feed line is controlled and the assembly of the antenna into a housing is reliable, resulting in repeatable antenna properties. However, other suitable attachment mechanisms are also be possible and known to those practiced in the art. While ground plane 360 is illustrated as along an edge of rigid portion 310, it is also possible that ground plane 360 is part of rigid portion 310, in one embodiment, part of flexible portion 320, in another embodiment, or extends across both, in yet another embodiment.

Figure 4:
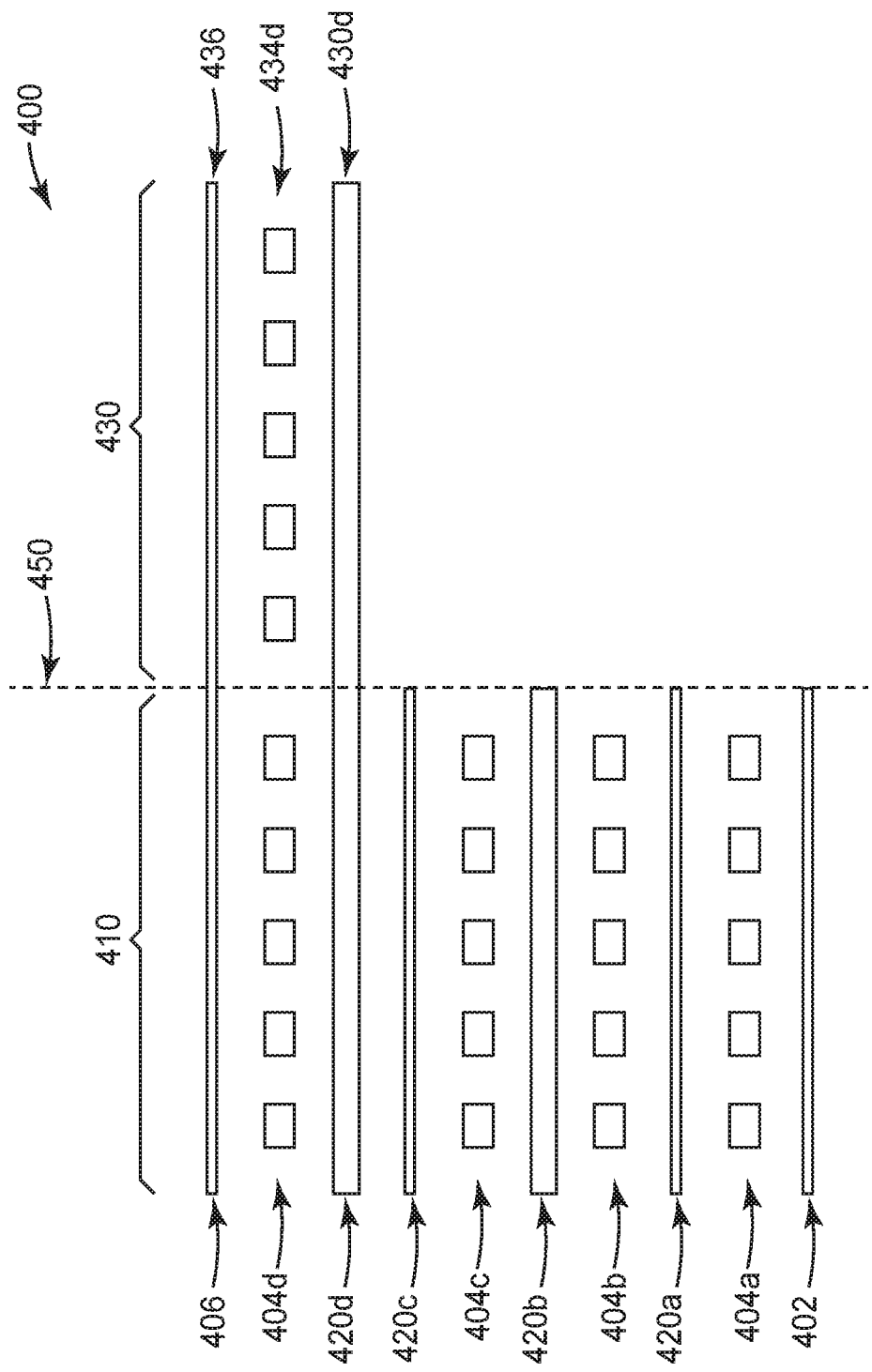
FIG. 4 illustrates a preferred layer diagram for construction of a headset antenna in accordance with a preferred embodiment of the invention.

FIG. 4 illustrates a schematic for construction of a headset antenna in accordance with an embodiment of the present invention. Antenna 400 includes as rigid portion 410 and a flexible portion 420. Each of portions 410 and 420 are made of different layers laminated together. A bottom solder layer 402 is opposed a top layer 406, 436. Top layer 406, 436 and bottom layer 402 are configured to support placement of surface mounted devices (SMD), such as a circuit and radio-frequency (RF) chip. In the embodiment illustrated in FIG. 4, top layer 406, 436 extends over both rigid portion 410 and flexible portion 430. This allows for short electrical connections along plane defined by rigid portion 410. This is important for the performance of antennae 400.

In contrast, in embodiments where flexible portion 430 includes middle or bottom layers, instead of top layer 406, 436, vias connecting to an outer layer are required to connect antennae 400 to components. While feasible, this is disadvantageous and requires more complicated manufacturing steps. However, in an embodiment where RF components are embedded in a PCB stack, such construction might be possible.

Rigid layer includes a plurality of dielectric layers 420a-d. Dielectric layers 420a-d may be made of the same material, in one embodiment, or different materials. In a preferred embodiment, layer 420d is polyimide. While FIG. 4 illustrates four dielectric layers, it is expressly contemplated that some embodiments include more or fewer layers. For example, only 1, 2 or 3 dielectric layers may be present. Additionally, 5, 6, 8 or more layers may be present. While schematic 400 is not shown to scale, in one embodiment it does depict thicknesses of internal layers to scale. However, in another embodiment, thicknesses are also not drawn to scale.

Layers including electrically conductive patterns 404a-404d are laminated in between dielectric layers 420a-d. Conductive layers 404a-404d are illustrated as discrete blocks, but are not indicative of the design plan of conductive layers 404a-404d. In one embodiment, the conductive pattern is formed using copper. However, in other embodiments, a different conductive material is used to form an electrically conductive pattern.

In a preferred embodiment, rigid portion 410 is manufactured such that layers 434d, 430d and 436 extend from layers 404, 410d and 406, respectively. However, in some embodiments any of these layers may be manufactured separately and later connected.

Along the edge of rigid portion 410, in one embodiment, extends a ground plane 450. It is important that, while flexible portion 430 is able to move and bend, it not be bent such that any of it crosses ground plane 450. In preferred embodiments, flexible portion 430 remains substantially planar after installation and during operation as well. However, while ground plane 450 is illustrated as along the edge of rigid portion 410 in FIG. 4, in other embodiments it can be positioned elsewhere. For example, ground plane 450 may be located anywhere within the rigid portion 410, in one embodiment. In another embodiment, ground plane 450 is located within flexible portion 430. In a further embodiment, ground plane 450 extends between rigid portion 410 and flexible portion 430.

Construction of antennae 400 as illustrated in the schematic of FIG. 4 allows for a robust design with reliable electrical connection between rigid portion 410 and flexible portion 420, which results in steady antenna performance. Additionally, because solder is not used for connections, antenna performance is repeatable from manufactured antenna to antenna. Additionally, lamination of layers simplifies the assembly process of antenna 400 as compared to conventional wire or metal sheet antennae which requires more parts. Further, because screws and solder are not needed to place the flexible portion 430 of antenna system 400, manufacturing is also cheaper because manual labor is not required.

Figure 5:
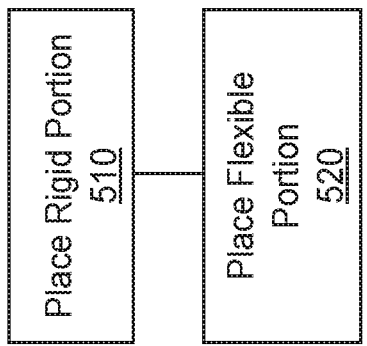
FIG. 5 illustrates a preferred embodiment of method of headset antenna placement in accordance with a preferred embodiment of the present invention.

FIG. 5 illustrates a method of placing a headset antenna in accordance with an embodiment of the present invention. Method 500 applies, in one embodiment, to placement of a headset antenna within a housing of a hearing protection device. In one embodiment, the hearing protection device is a headset with two earmuff portions coupled by a headband. In one embodiment, only one of the two earmuff portions includes an antennae, and method 500 is performed once during manufacturing of a headset. In another embodiment, each of the two earmuff portions includes an antenna.

In step 510, a rigid portion of an antenna is placed. Placement of the rigid portion is accomplished mechanically, in one embodiment, using screws. However, other non-solder based fixing mechanisms may also be used, in other embodiments. In one embodiment, three screws are used to fix the rigid portion of the antenna. However, more, or fewer, screws may be necessary in other embodiments. For example, only one screw, or two screws, or four screws, or more. Additional suitable attachment mechanisms also envisioned. For example, the rigid portion may be held in place by applied pressure. The applied pressure may come directly from the housing, or from an insert between the housing and the rigid portion. For example, a foam insert may compress between the housing and the rigid portion, causing an applied pressure. In another embodiment, one or more hooks are used to hold the rigid portion in place. Additionally, in some embodiments an insert is present between the rigid portion and the housing.

In step 520, a flexible portion of an antenna is placed. In one embodiment, this includes bending parts of the flexible portion of the antenna such that flexible portion conforms to an inner housing of an earmuff. However, the flexible portion of the antenna is configured such that it does not cross a ground plane that is substantially along the edge of the rigid portion. Placement of flexible portion is accomplished, in one embodiment, using adhesive tape. However, other non solder-based attachment mechanisms are also envisioned. For example, applied pressure may keep the flexible portion in place within the housing in one embodiment. In another embodiment an insert or an interface may be present within the housing that serves to keep the flexible portion in place.

In one embodiment, once placed, rigid and flexible portions remain substantially planar with respect to each other within a headset. The flexible portion, in one embodiment, is next to a ground plane. In another embodiment, the flexible portion is within the same plane as the ground plane.

Figure 6:
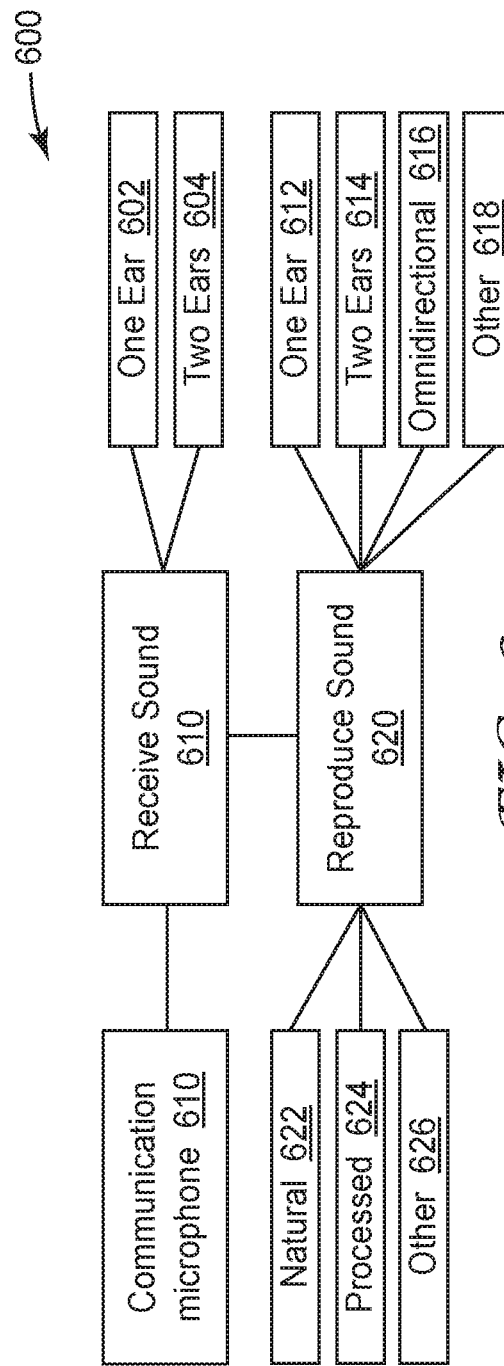
FIG. 6 illustrates a method of using a headset antenna in accordance with an embodiment of the present invention.

FIG. 6 illustrates a method of using a headset antenna in accordance with an embodiment of the present invention. Method 600 may be useful for a headset antenna within a hearing protection device. A hearing protection device is designed to dampen ambient sound for a user. Microphones are configured to receive ambient sound, and the hearing protection device is configured to process the ambient sound to a safe level for a user. An antenna, such as the antennae described with respect to FIGS. 2-4, is used for receiving Radio frequency (RF) signals and processing them to reproduce sound for a user such that the sound accurately reflects a distance between the wearer of the hearing protection device and the transceiver antenna at source of the sound. This requires an antenna that allows the hearing protection device to operate within an NIB environment. Such an antenna may need to function omnidirectionally.

In block 610, ambient sound is received Ambient sound may be received by a microphone, in one embodiment. A microphone may be located in one earpiece, as indicated in block 602, or in both earpieces of a headset, as indicated in block 604. Sounds from the user are also captured by microphone 605. Sound from another user of a similar hearing protection device may be demodulated by a transceiver after being picked up by an antenna.

In block 620, reproduced sound is provided to a user. Sound may be reproduced in only one earmuff, as indicated in block 612, or in both earmuffs, as indicated in block 614. If a suitable antenna is present that is capable of allowing a headset to detect distance and direction of a sound, reproduced sound may also be provided such that it sounds omnidirectional, instead of from only two speakers. Other features may also be present, in other embodiments.

The reproduced sound may be provided such that it is not altered, as indicated in block 622. In another embodiment, the sound is processed, as indicated in block 624, for example to reduce the sound to a safe level for a user to hear. The reproduced sound may also have other features.

Figure 7B:
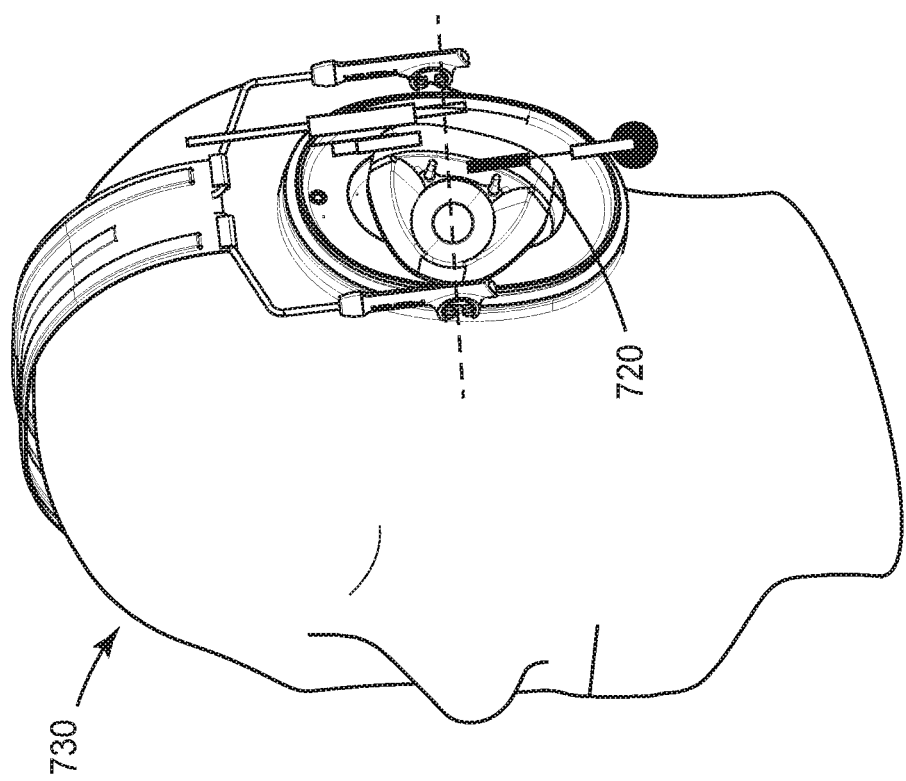
FIGS. 7A-7C illustrate potential placement of a headset antenna in two embodiments of the system and resulting potential polar patterns.
Figure 7A:
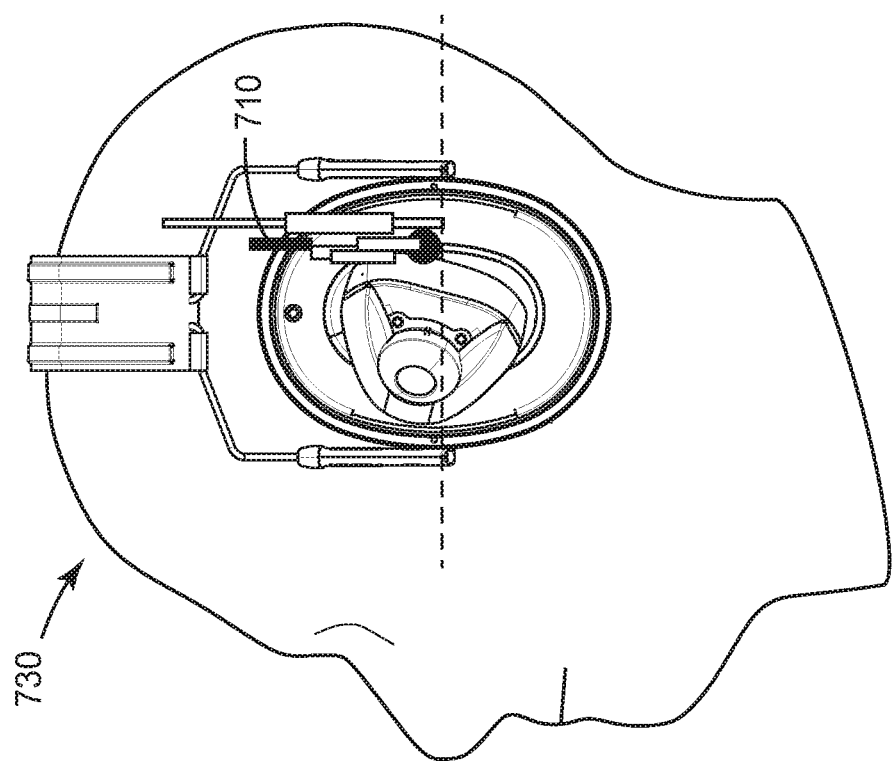
Figure 7C:
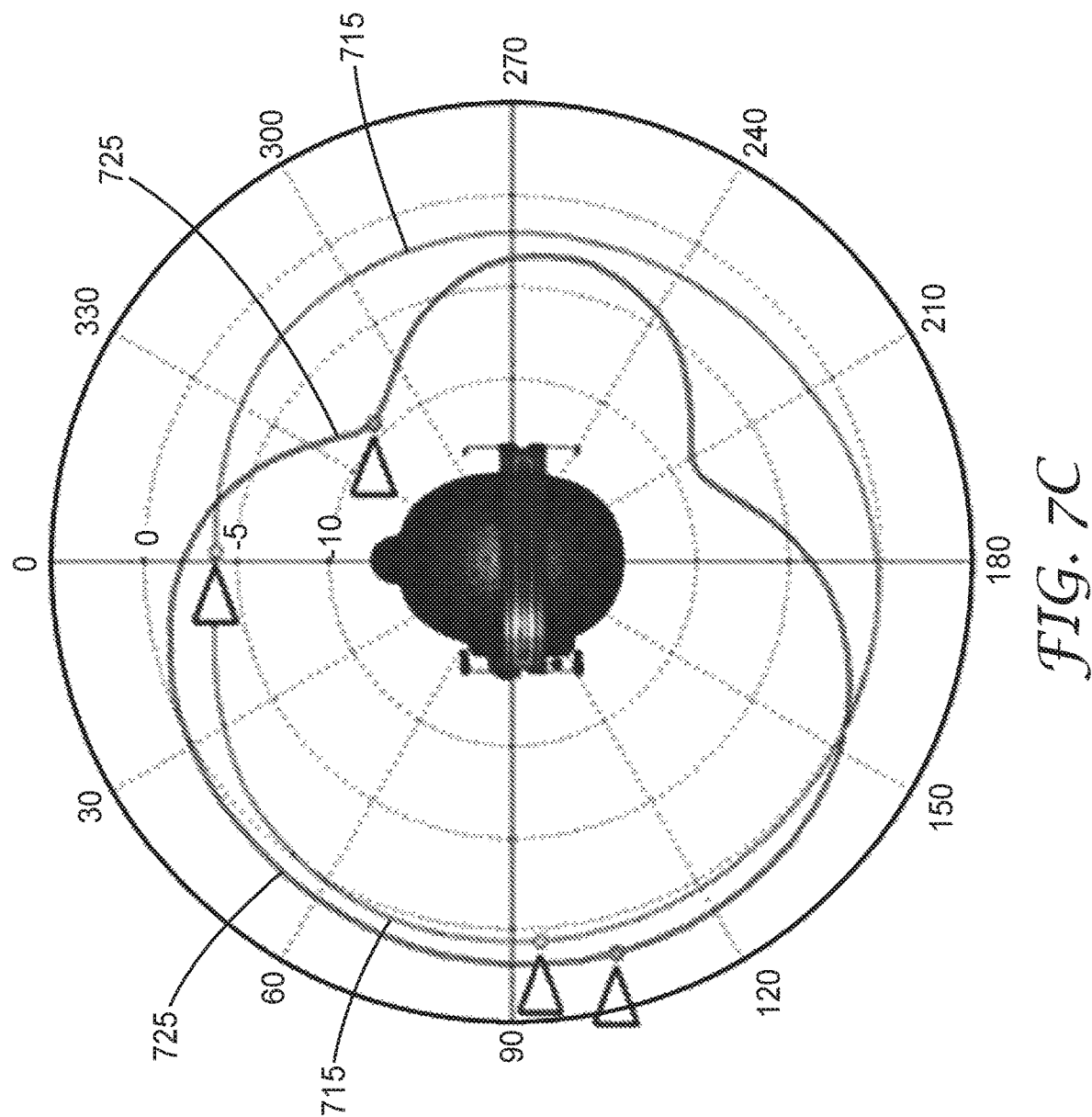

FIGS. 7A-7C illustrate potential placements of a headset antenna in two embodiments of the system and resulting potential polar patterns.

EMBODIMENTS

Embodiment 1 is a hearing protection device. The hearing protection device includes a first earmuff connected to a second earmuff by a headband. Each of the first and second earmuffs are configured to dampen ambient sound. The hearing protection device also includes an antenna, located within a housing of the first earmuff. The antenna includes a rigid portion coupled to a flexible portion. Both the rigid portion and the flexible portion are fixed within the housing using an attachment mechanism.

Embodiment 2 includes the features of embodiment 1, however, wherein the antenna remains substantially planar within the housing.

Embodiment 3 includes the features of any of embodiments 1-2, however the rigid portion is fixed within the housing by a screw.

Embodiment 4 includes the features of any of embodiments 1-3, however the rigid portion is fixed within the housing by a plurality of screws.

Embodiment 5 includes the features of any of embodiments 1-4, however the flexible portion is fixed within the housing by an adhesive.

Embodiment 6 includes the features of any of embodiments 1-5, however the attachment mechanism includes applied pressure.

Embodiment 7 includes the features of any of embodiments 1-6, however the attachment mechanism includes an interface between the housing and one of the rigid and flexible portions.

Embodiment 8 includes the features of any of embodiments 1-7, however the rigid portion includes a plurality of laminated layers.

Embodiment 9 includes the features of any of embodiments 1-8, however the flexible portion includes a subset of the plurality of layers.

Embodiment 10 includes the features of embodiment 9, however the subset of layers including the flexible portion extend from the rigid portion.

Embodiment 11 includes the features of embodiment 8, however the plurality of laminated layers includes at least one dielectric and at least one conductive layer.

Embodiment 12 includes the features of embodiment 11, however one of the dielectric layers includes polyimide.

Embodiment 13 includes the features of embodiment 8, however the plurality of laminated layers includes at least one layer including electrically conductive layer patterns.

Embodiment 14 includes the features of embodiment 9, however the flexible portion includes at least one layer comprising electrically conductive patterns.

Embodiment 15 includes the features of embodiment 9, however the flexible portion includes a dielectric layer.

Embodiment 16 includes the features of any of embodiments 1-15, however a ground plane is located along an edge of the rigid portion.

Embodiment 17 includes the features of any of embodiments 1-16, however the flexible portion is adjacent to a ground plane.

Embodiment 18 includes the features of embodiment 17, however the flexible portion does not cross the ground plane.

Embodiment 19 includes the features of any of embodiments 1-18, however the flexible portion is substantially in line with the ground plane.

Embodiment 20 includes the features of any of embodiments 1-19, however the antenna is positioned within the housing such that the headset can detect a signal strength of a received RF signal and use the detected signal strength to determine the distance from the received RF signal, such that the received sound can be attenuated.

Embodiment 21 includes the features of any of embodiments 1-20, however the antenna is positioned within the top half of the earmuff housing.

Embodiment 22 includes the features of any of embodiments 1-21, however it also includes a second antenna located within the second earmuff.

Embodiment 23 includes the features of embodiment 22, however it also includes an electrical connection between the first and second earmuff.

Embodiment 24 includes the features of any of embodiments 1-23, however the rigid portion is fixed within the housing by an applied pressure.

Embodiment 25 includes the features of any of embodiments 1-24, however the rigid portion is fixed within the housing using an insert.

Embodiment 26 is a headset. The headset includes a first over-the-ear hearing device and a second over-the-ear hearing device. Each device includes a speaker configured to provide sound at a safe level to a wearer. The headset also includes an antenna positioned in a housing of the first over-the-ear hearing device. The antenna includes a rigid portion and a flexible portion. The rigid and flexible portions are fixed in place within the housing. The flexible portion is substantially in line with a ground plane of the antenna.

Embodiment 27 includes the features of embodiment 26, however the rigid portion includes a plurality of laminated layers.

Embodiment 28 includes the features of embodiment 27, however the plurality of laminated layers includes a dielectric layer.

Embodiment 29 includes the features of embodiment 27, however one of the plurality of layers includes polyimide.

Embodiment 30 includes the features of embodiment 27, however the plurality of laminated layers includes at least one layer including electrically conductive layer patterns.

Embodiment 31 includes the features of embodiment 27, the flexible portion includes a subset of the plurality of laminated layers.

Embodiment 32 includes the features of embodiment 31, however the subset of layers including the flexible portion extend from the rigid portion.

Embodiment 33 includes the features of any of embodiments 26-32, however the antenna is substantially planar.

Embodiment 34 includes the features of any of embodiments 26-33, however it also includes a second antenna in the second over-the-ear device.

Embodiment 35 includes the features of any of embodiments 26-34, however the antenna is completely within the housing.

Embodiment 36 includes the features of any of embodiments 26-35, however the rigid portion is fixed in place using at least one screw.

Embodiment 37 includes the features of any of embodiments 26-36, however the rigid portion is fixed in place by an applied pressure.

Embodiment 38 includes the features of any of embodiments 26-37, however it also includes an insert between the rigid portion and the housing.

Embodiment 39 includes the features of any of embodiments 26-38, however the flexible portion is fixed in place using adhesive.

Embodiment 40 is an antenna configured for placement within a housing of a personal protective equipment. The antenna includes a rigid portion comprising a plurality of laminated layers. The antenna also includes a flexible portion comprising a subset of the plurality of layers. The antenna also includes a ground plan. The flexible portion and the ground plane are substantially coplanar.

Embodiment 41 includes the features of embodiment 40, however the rigid portion and flexible portion are substantially coplanar.

Embodiment 42 includes the feature of any of embodiments 40-41, however the ground plane is part of the rigid portion.

Embodiment 43 includes the features of any of embodiments 40-42, however the ground portion is located along an edge of the rigid portion.

Embodiment 44 includes the features of any of embodiments 40-43, however the plurality of layers includes a dielectric layer.

Embodiment 45 includes the features of any of embodiments 40-44, however one of the plurality of layers is polyimide.

Embodiment 46 includes the features of any of embodiments 40-45, however the plurality of laminated layers has at least one layer including electrically conductive layer patterns Embodiment 47 includes the features of any of embodiments 40-46, however the antenna is configured to fit completely within the housing.

Embodiment 48 includes the features of any of embodiments 40-47, however the rigid portion is configured to be fixed in place within the housing using an attachment mechanism.

Embodiment 49 includes the features of embodiment 48, however the attachment mechanism is a screw.

Embodiment 50 includes the features of embodiment 40, however the attachment mechanism is an applied pressure.

Embodiment 51 includes the features of embodiment 48, however the attachment mechanism includes a hook.

Embodiment 52 includes the features of embodiment 48, however the attachment mechanism includes an interface between the housing and the rigid portion.

Embodiment 53 includes the features of embodiment 48, however the attachment mechanism includes an insert.

Embodiment 54 includes the features of any of embodiments 40-53, however the flexible portion is configured to be fixed in place using adhesive.

Embodiment 55 is a method of installing an antenna within a headset. The method includes fixing a rigid portion of the antenna within a housing of an over-the-ear muff of the headset. The method also includes fixing a flexible portion of the antenna within the housing. Once fixed, the rigid and flexible portions remain in place within the housing. Once fixed, the flexible portion remains coplanar with a ground plane.

Embodiment 56 includes the features of embodiment 55, however fixing the flexible portion includes bending the flexible portion.

Embodiment 57 includes the features of any of embodiments 55-56, however the flexible portion is adjacent to the ground plane.

Embodiment 58 includes the features of any of embodiments 55-57, however the antenna is fixed completely within the housing.

Embodiment 59 includes the features of any of claims 55-58, however fixing the flexible portion includes applying an adhesive.

Embodiment 60 includes the features of any of embodiments 55-59, however fixing the rigid portion includes applying a pressure.

Embodiment 61 includes the features of any of embodiments 55-60, however fixing the rigid portion includes an attachment mechanism.

Embodiment 62 includes the features of embodiment 61, however the attachment mechanism includes at least one screw.

Embodiment 63 includes the features of embodiment 61, however the attachment mechanism includes an interface between the housing and the rigid portion.

Embodiment 64 includes the features of embodiment 61, however the attachment mechanism includes an insert between the housing and the rigid portion.

EXAMPLES

Various embodiments of the present disclosure can be better understood by reference to the following Examples which are offered by way of illustration. The present disclosure is not limited to the Examples given herein.

Example 1

FIGS. 7A-7C illustrate potential placement of a headset antenna and resulting RF polar pattern for Examples 1 and 2.

To find the right type of antenna and the right position for the antenna, several steps were taken.

Using mechanical and material models, a 3-dimensional electro-magnetic simulation was deployed to determine the optimal position for the antenna in relation to the hearing device's earmuff. This simulation was used to evaluate several types of antennas in many positions. The antenna performance was evaluated based on polar patterns of the antenna gain to identify the best position. Those polar patterns were the result of the numerous electro-magnetic simulations.

The simulation setup comprised the hearing device (FIG. 1A, 100), several antennas (e.g. FIG. 7A, 710), and a dummy head (FIG. 7A, 730) to represent the human head. The material properties of the dummy head resemble those of the human head to consider its influence on the spatial antenna gain.

In a first step, the complete earmuff was evaluated for antenna performance. Simulation showed that the upper half of the earmuff is the most suitable for the antenna to achieve an omnidirectional gain pattern. FIG. 7A, 710 indicates one embodiment of the antenna in a well-performing position in the upper half of the earmuff.

To compare the numerous locations evaluated in simulation, a normal-mode helical antenna type was used. FIG. 7A, 710 depicts such an antenna in an advantageous position in the upper half of the earmuff resulting in a gain pattern close to being omnidirectional.

Example 2

The corresponding gain pattern for 720 is shown in FIG. 7C, 715. FIG. 7B, 720 depicts a normal-mode helical antenna in a disadvantageous position in the lower half of the earmuff.

The resulting gain pattern is shown in FIG. 7C, 725. Comparing 715 with 725, the disadvantage is apparent as 725 deviates strongly from the ideal. However, 715 shows less deviation from the ideal than 725.

Example 3

Figure 8:
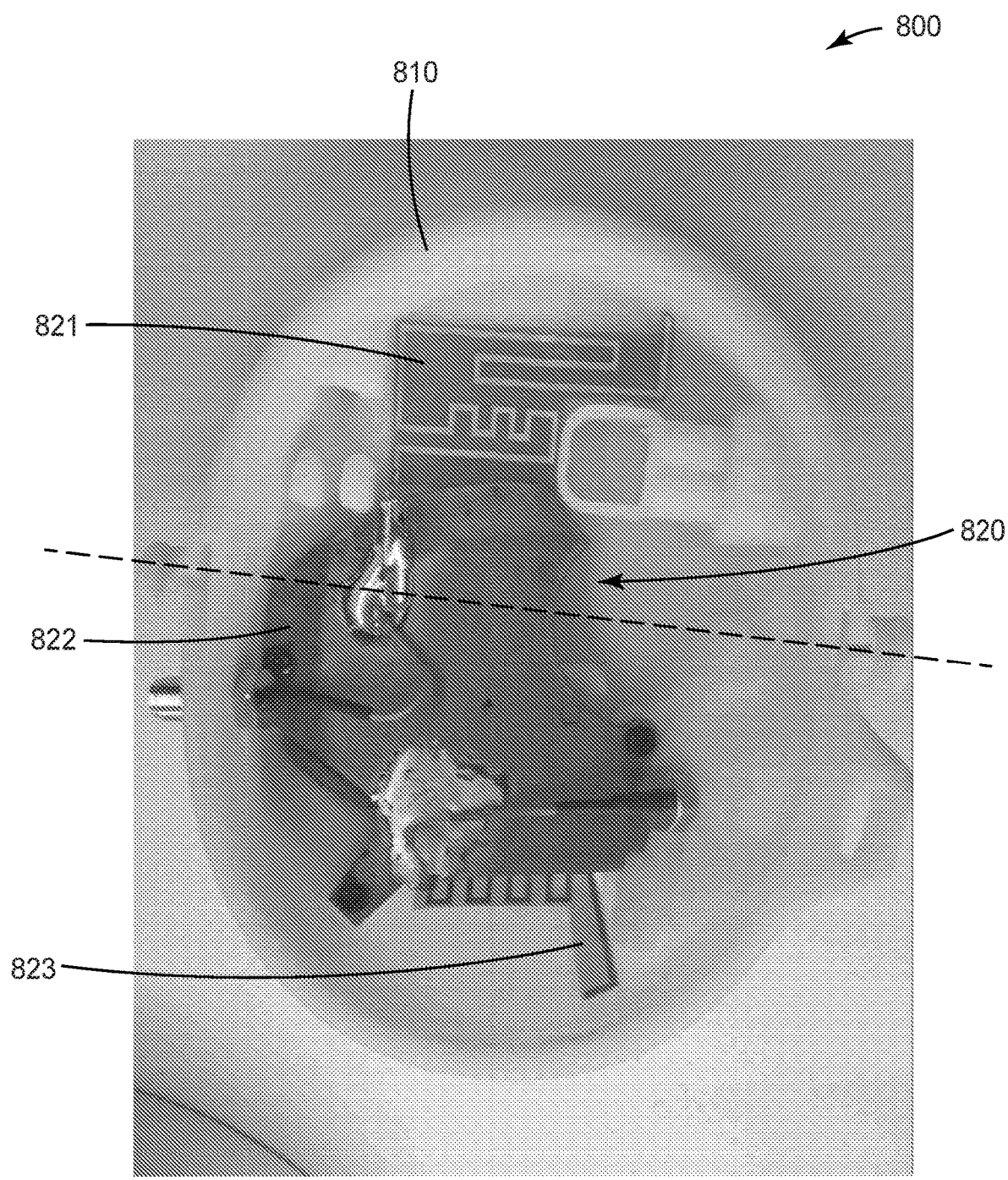
FIG. 8 illustrates a preferred embodiment of a headset antenna in accordance with a further preferred embodiment of the present invention.

After determining antenna type and preferred location in relation to the earmuff using 3-dimensional electro-magnetic simulations, a prototype was created to verify the simulation results (FIG. 8, 800).

From the simulation results, a planar antenna delivered the best performance. Several embodiments of planar antennas were evaluated, one such embodiment is shown in FIG. 2, 230, another embodiment is shown in FIG. 8, 820 and yet another embodiment is shown in FIG. 8, 840.

The prototype 800 consists of earmuff 810 and antenna system 820. The antenna system comprises rigid portion 822 and 2 flexible portions 821 and 823. The rigid portion 822 further includes a ground plane. Flexible portion 821 is located in the upper half of the earmuff, while flexible portion 823 is located in the lower half. For the measurements, prototype 800 was attached to a headband and a second earmuff to form a complete headset similar to FIG. 1A, 100.

The flexible portion 821 of the prototype is in a comparable location to antenna 710 of FIG. 7A, whereas flexible portion 823 is in a comparable location to antenna 720 of FIG. 7B.

The measurement results from prototype 800 attached to the dummy head, second earmuff and headband correlate with the simulation results: The performance of flexible portion 821 correlates with results 715 and the performance of flexible portion 823 correlates with results 725.

What is claimed is:

1. A hearing protection device comprising:
   a first earmuff connected to a second earmuff by a connector, wherein each of the first and second earmuffs are configured to dampen ambient sound; and
   an antenna, located within a housing of the first earmuff, wherein the antenna comprises:

a rigid portion coupled to a flexible portion, wherein both the rigid portion and the flexible portion are fixed within the housing using an attachment mechanism; and wherein the rigid portion comprises a plurality of laminated layers, and wherein the plurality of laminated layers comprises at least one dielectric and at least one conductive layer.

2. The hearing protection device of claim 1, wherein the antenna remains substantially planar within the housing.

3. The hearing protection device of claim 1, wherein the attachment mechanism comprises applied pressure.

4. The hearing protection device of claim 1, wherein the attachment mechanism comprises an interface between the housing and one of the rigid and flexible portions.

5. The hearing protection device of claim 1, wherein the flexible portion comprises a subset of the plurality of layers.

6. The hearing protection device of claim 5, wherein the subset of layers comprising the flexible portion extend from the rigid portion.

7. The hearing protection device of claim 1, wherein the plurality of laminated layers comprises at least one layer including electrically conductive layer patterns.

8. The hearing protection device of claim 5, wherein the flexible portion comprises at least one layer comprising electrically conductive patterns.

9. The hearing protection device of claim 5, wherein the flexible portion comprises a dielectric layer.

10. The hearing protection device of claim 1, wherein a ground plane is located along an edge of the rigid portion.

11. The hearing protection device of claim 1, wherein the antenna is positioned within the housing such that the headset can detect a signal strength of a received RF signal and use the detected signal strength to determine the distance from the received RF signal, such that the received sound can be attenuated.

12. The hearing protection device of claim 1, wherein the rigid portion is fixed within the housing by an applied pressure.

13. The hearing protection device of claim 1, wherein the rigid portion is fixed within the housing using an insert.

14. A hearing protection device comprising:
a first earmuff connected to a second earmuff by a connector, wherein each of the first and second earmuffs are configured to dampen ambient sound; and
an antenna, located within a housing of the first earmuff, wherein the antenna comprises:
a rigid portion coupled to a flexible portion, wherein both the rigid portion and the flexible portion are fixed within the housing using an attachment mechanism; and
wherein the rigid portion comprises a plurality of laminated layers, and wherein the plurality of laminated layers comprises at least one layer including electrically conductive layer patterns.

15. The hearing protection device of claim 14, wherein the antenna is positioned within the housing such that the headset can detect a signal strength of a received RF signal and use the detected signal strength to determine the distance from the received RF signal, such that the received sound can be attenuated.

16. A hearing protection device comprising:
a first earmuff connected to a second earmuff by a connector, wherein each of the first and second earmuffs are configured to dampen ambient sound; and
an antenna, located within a housing of the first earmuff, wherein the antenna comprises:
a rigid portion coupled to a flexible portion, wherein both the rigid portion and the flexible portion are fixed within the housing using an attachment mechanism; and
wherein the antenna is positioned within the housing such that the headset can detect a signal strength of a received RF signal and use the detected signal strength to determine the distance from the received RF signal, such that the received sound can be attenuated.

17. The hearing protection device of claim 16, wherein the rigid portion comprises a plurality of laminated layers, and wherein the plurality of laminated layers comprises at least one layer including electrically conductive layer patterns.

18. The hearing protection device of 16, wherein the flexible portion comprises a subset of the plurality of layers.

19. The hearing protection device of claim 18, wherein the subset of layers comprising the flexible portion extend from the rigid portion.

20. The hearing protection device of 16, wherein the plurality of laminated layers comprises at least one layer including electrically conductive layer patterns.

* * * * *